US008534456B2

(12) United States Patent
Kimura et al.

(10) Patent No.: US 8,534,456 B2
(45) Date of Patent: Sep. 17, 2013

(54) CONVEYOR DEVICE FOR ANALYZER, ANALYZER, ANALYZING SYSTEM, AND CONNECTOR FOR CONVEYOR DEVICE

(75) Inventors: Masahiro Kimura, Kyoto (JP); Kazuhiko Okuda, Kyoto (JP); Masayuki Kubo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 479 days.

(21) Appl. No.: 12/919,852

(22) PCT Filed: Feb. 28, 2009

(86) PCT No.: PCT/JP2009/053774
§ 371 (c)(1),
(2), (4) Date: Aug. 27, 2010

(87) PCT Pub. No.: WO2009/107817
PCT Pub. Date: Sep. 3, 2009

(65) Prior Publication Data
US 2011/0000763 A1  Jan. 6, 2011

(30) Foreign Application Priority Data

Feb. 29, 2008 (JP) .................................. 2008-051393
Mar. 21, 2008 (JP) .................................. 2008-074508
Mar. 21, 2008 (JP) .................................. 2008-074509

(51) Int. Cl.
*G01N 35/04* (2006.01)
*B65G 21/00* (2006.01)
(52) U.S. Cl.
USPC .................. 198/860.1; 198/860.2; 198/861.1; 198/539; 198/950

(58) Field of Classification Search
USPC ................ 198/539, 583, 860.1, 860.2, 860.3, 198/860.5, 861.1, 950
See application file for complete search history.

(56) References Cited

U.S. PATENT DOCUMENTS

| 4,792,270 | A | * | 12/1988 | Yoshida ......................... 414/273 |
| 4,824,311 | A | * | 4/1989 | Mims ............................ 414/273 |
| 4,863,319 | A | * | 9/1989 | Winkler et al. ................ 409/134 |
| 5,406,772 | A | * | 4/1995 | Dinius ............................. 53/67 |
| 5,531,004 | A | * | 7/1996 | Ahn ............................... 29/33 P |
| 5,617,945 | A | * | 4/1997 | Takahashi et al. .......... 198/471.1 |
| 6,058,159 | A | * | 5/2000 | Conway et al. .................. 378/68 |
| 6,170,649 | B1 | * | 1/2001 | Radandt et al. ............. 198/860.1 |

(Continued)

FOREIGN PATENT DOCUMENTS

| JP | 3-285174 | 12/1991 |
| JP | 1994-341995 A | 12/1994 |

(Continued)

*Primary Examiner* — Douglas Hess
(74) *Attorney, Agent, or Firm* — Morgan, Lewis & Bockius LLP

(57) ABSTRACT

A conveyor device 2 for analyzer includes: a conveyance tracks 20A and 20B capable of conveying a specimen rack 3 along a fixed path; and a frame 21 positioned around the conveyance tracks 20A and 20B, the frame 21 being provided with separable and removable portions 24A and 24B which are separable and removable from the frame 21 and which are capable of providing the frame 21 with cutouts in open condition when separated and removed from the frame 21. When the frame 21 is provided with the cutouts in open condition, the cutouts allows the specimen rack 3 to be introduced onto and discharged from the conveyance tracks 20A and 20B from outer lateral sides of the frame 21 through the cutouts.

10 Claims, 15 Drawing Sheets

(56) References Cited

U.S. PATENT DOCUMENTS

| | | | |
|---|---|---|---|
| 6,238,161 B1 * | 5/2001 | Kirkpatrick et al. | 414/217 |
| 6,325,202 B1 * | 12/2001 | Gaines | 198/583 |
| 6,510,935 B1 * | 1/2003 | McIlvaine | 193/35 R |
| 6,669,430 B2 * | 12/2003 | Ostwald et al. | 414/277 |
| 6,698,583 B2 * | 3/2004 | Itoh | 198/860.4 |
| RE38,517 E * | 5/2004 | Pfeiffer et al. | 414/276 |
| 7,500,556 B2 * | 3/2009 | Lemke et al. | 198/861.1 |
| 8,062,591 B2 * | 11/2011 | Yamamoto | 422/63 |
| 8,357,538 B2 * | 1/2013 | Self et al. | 436/47 |
| 2002/0025064 A1 | 2/2002 | Itoh | 382/134 |

FOREIGN PATENT DOCUMENTS

| | | |
|---|---|---|
| JP | 07-092171 | 4/1995 |
| JP | 1997-243645 A | 9/1997 |
| JP | 1998-014682 A | 1/1998 |
| JP | 1998-090277 A | 4/1998 |
| JP | 1998-282111 A | 10/1998 |
| JP | 1998-282114 A | 10/1998 |
| JP | 1999-148940 A | 6/1999 |
| JP | 1999-316238 A | 11/1999 |
| JP | 2000-055924 A | 2/2000 |
| JP | 2001-349897 A | 12/2001 |
| JP | 2002-5942 | 1/2002 |
| JP | 3616744 | 2/2005 |

* cited by examiner

CONVEYOR DEVICE FOR ANALYZER, ANALYZER, ANALYZING SYSTEM, AND CONNECTOR FOR CONVEYOR DEVICE

RELATED APPLICATIONS

This application is a 371 filing based on PCT/JP2009/053774, filed Feb. 28, 2009, which claims priority to Japanese Application No. 2008-051393, filed Feb. 29, 2008; Japanese Application No. 2008-074508, filed Mar. 21, 2008; and Japanese Application No. 2008-074509, filed Mar. 21, 2008, all of which are hereby incorporated by reference in their entirety.

TECHNICAL FIELD

The present invention relates to: a conveyor device for analyzer for use in conveying a specimen rack along a predetermined path; an analyzer provided with the same; an analyzing system; and a connector for such a conveyor device for analyzer. The "specimen rack", as used in the present invention, is a rack for supporting one or more containers each containing a specimen such as blood or urine.

BACKGROUND ART

Among conventional analyzers for analyzing specimens such as blood and urine, there is an analyzer of the type having an analyzer body which is capable of analyzing a specimen and which is combined with a conveyor device designed to convey a specimen rack along a fixed path. With this construction, it is possible to automate an operation to convey a plurality of specimen racks sequentially to a predetermined point in the analyzer body, thereby to facilitate and speed-up the specimen analyzing operation.

In some cases, instead of being used solely, an analyzer is used as connected to another analyzer for a specimen rack to be passed between these analyzers (see Patent Documents 1 and 2 for example). With such an arrangement, analyzing operations for plural items of analysis can be performed continuously, thus resulting in a highly efficient analyzing operation.

Conventionally, however, there is room for improvements as described below.

That is, since an analyzer may be used not only solely but also as combined with another analyzer as described above, such an analyzer is requested to have an arrangement capable of suitably accommodating to the latter case also. In order to meet such a request suitably, the conveyor device incorporated in one analyzer is required to be easily connectable to the conveyor device of another analyzer so as to allow a specimen rack to be properly passed between the two analyzers.

Heretofore, no proposal has been made of a conveyor device for analyzer which is capable of meeting the aforementioned request suitably. Typically, a conventional conveyor device for analyzer has an arrangement provided with a frame positioned around a conveyance track for specimen rack. The frame can be utilized as a guide for the conveyance of specimen racks. The frame is also useful in preventing articles other than specimen racks from inadvertently approaching onto the conveyance track. In connecting a pair of conveyor devices each having such an arrangement, however, it is difficult for a specimen rack to be properly passed between the pair of conveyor devices because the frames interfere with the passage of the specimen rack. For this reason, the conventional art cannot easily realize combined use of an analyzer that has been used solely and another analyzer or the like, thus causing an inconvenience.

Patent Document 1: Japanese Patent Publication No. 3616744
Patent Document 2: Japanese Patent Laid-Open Publication No. HEI7-92171

DISCLOSURE OF THE INVENTION

Problems to be Solved by the Invention

An object of the present invention is to provide: a conveyor device for analyzer which is capable of properly eliminating or alleviating the foregoing problem; an analyzer provided with the same; an analyzing system; and a connector for conveyor device.

Means for Solving the Problems

In order to solve the foregoing problem, the present invention provides the following technical means.

According to a first aspect of the present invention, there is provided a conveyor device for analyzer comprising: a conveyance track capable of conveying a specimen rack along a fixed path; and a frame positioned around the conveyance track, the frame being provided with a separable and removable portion which is separable and removable from the frame and which is capable of providing the frame with a cutout in open condition when separated and removed from the frame, wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout.

Preferably, the conveyor device has an arrangement wherein: the frame is provided with a pair of vertically extending slits which are horizontally spaced apart from each other to provide a brittle portion of the frame therebetween; and the brittle portion forms the separable and removable portion.

Preferably, the conveyor device has an arrangement wherein: the frame is fitted with a separate and removable closing member in such a manner as to close a cutout previously formed in the frame; and the closing member forms the separable and removable portion.

Preferably, the conveyor device has an arrangement wherein: the conveyance track has a starting area located close to a first widthwise end of the frame and an ending area located close to an opposite second widthwise end of the frame; the separable and removable portion is provided at each of the first and second widthwise ends of the frame to enable a first cutout to be formed at the first widthwise end of the frame for allowing the specimen rack to advance therethrough into the starting area from a first outer lateral side of the frame and enable a second cutout to be formed at the second widthwise end of the frame for allowing the specimen rack to be discharged therethrough from the ending area to a second outer lateral side of the frame.

Preferably, the conveyor device for analyzer according to the present invention further comprises a connector which is capable of connecting the frame to another conveyor device for analyzer and which has an upwardly oriented guide surface capable of guiding the specimen rack being conveyed through the first cutout or the second cutout when the connector is in a connecting state.

Preferably, the conveyor device for analyzer according to the present invention further comprises a movable member which is reciprocable widthwise of the frame at a location adjacent the ending area, the movable member being capable of moving the specimen rack having been conveyed into the ending area toward the second cutout.

Preferably, the movable member is capable of advancing onto the guide surface from the ending area side when the connector is connected to the frame to guide the specimen rack passing through the second cutout.

Preferably, the conveyor device has an arrangement wherein: the separable and removable portion is fitted with a sensor for detecting whether or not the specimen rack is present at a predetermined point; and when the separable and removable member is separated and removed from the frame, the sensor is allowed to be removed from the separable and removable member and then placed adjacent the predetermined point for reuse in determination as to whether or not the specimen rack is present at the predetermined point.

According to a second aspect of the present invention, there is provided an analyzer comprising a conveyor device, the conveyor device comprising: a conveyance track capable of conveying a specimen rack along a fixed path; and a frame positioned around the conveyance track, the frame being provided with a separable and removable portion which is separable and removable from the frame and which is capable of providing the frame with a cutout in open condition when separated and removed from the frame, wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout.

Preferably, the analyzer according to the present invention includes: an analyzer body capable of analyzing a specimen; a conveyor device capable of conveying the specimen rack having been fed into a predetermined starting area toward the analyzer body or a location adjacent thereto and then conveying the specimen rack to a predetermined ending area; and control means having a signal input/output section capable of data communication with another analyzer, the control means being configured to carry out a process including: outputting a predetermined first signal from the signal output/input section to outside in response to arrival of a specimen rack at the ending area; instructing the conveyor device to perform an operation to discharge the specimen rack from the ending area to outside of the conveyor device in response to receipt of a predetermined second signal by the signal input/output section from outside after the outputting of the first signal; determining whether or not a predetermined condition for receiving a specimen rack into the starting area is satisfied in response to receipt of the first signal by the signal input/output section from outside; and outputting the second signal from the signal input/output section in response to a determination that the predetermined condition is satisfied.

Preferably, the predetermined condition is a condition in which any specimen rack is not present in the starting area of the conveyor device while the starting area is in a stationary condition incapable of conveying a specimen rack.

According to a third aspect of the present invention, there is provided an analyzing system comprising: a plurality of analyzers each provided with a conveyor device; and connector means designed to connect the plurality of analyzers to each other for allowing a specimen rack to be passed between the plurality of analyzers, the conveyor device comprising: a conveyance track capable of conveying the specimen rack along a fixed path; and a frame positioned around the conveyance track, the frame being provided with a separable and removable portion which is separable and removable from the frame and which is capable of providing the frame with a cutout in open condition when separated and removed from the frame, wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout, the analyzers each comprising: an analyzer body capable of analyzing a specimen; a conveyor device capable of conveying the specimen rack having been fed into a predetermined starting area toward the analyzer body or a location adjacent thereto and then conveying the specimen rack to a predetermined ending area; and control means having a signal input/output section capable of data communication with another analyzer, the control means being configured to carry out a process including: outputting a predetermined first signal from the signal output/input section to outside in response to arrival of a specimen rack at the ending area; instructing the conveyor device to perform an operation to discharge the specimen rack from the ending area to outside of the conveyor device in response to receipt of a predetermined second signal by the signal input/output section from outside after the outputting of the first signal; determining whether or not a predetermined condition for receiving a specimen rack into the starting area is satisfied in response to receipt of the first signal by the signal input/output section from outside; and outputting the second signal from the signal input/output section in response to a determination that the predetermined condition is satisfied.

Preferably, the analyzing system according to the present invention has an arrangement wherein: the plurality of analyzers include a first analyzer and a second analyzer designed to receive a plurality of specimen racks sequentially from the first analyzer and analyze specimens thereon; when a predetermined number of specimen racks are stopped on the conveyor device of the first analyzer due to the second analyzer in a condition disabled to receive a specimen rack, the first analyzer switches to a standby mode in which a specimen analyzing operation is suspended temporarily; and when the standby mode is established, a predetermined operation is performed for preventing a predetermined device or member utilized in the analyzing operation of the first analyzer from degrading in performance or quality during the standby mode.

Preferably, the analyzing system has an arrangement wherein: the first analyzer has a dispenser designed to take a specimen out of a container supported on each of the specimen racks and dispense the specimen to a predetermined portion for analysis; the dispenser has a nozzle cleaning function capable of supplying a cleaning liquid into a dispensing nozzle after the specimen has been sucked into and discharged from the nozzle by actuating a pump connected to the nozzle; and when the first analyzer switches to the standby mode, an air purge operation for supplying the cleaning liquid into the nozzle is performed by actuating the pump by the time at which the standby mode is released thereafter to cause the dispenser to restart taking the specimen out of the container.

Preferably, the air purge operation is performed only when the duration of the standby mode is longer than a predetermined time period.

Preferably, the air purge operation starts at the time at which the duration of the standby mode reaches the predetermined time period.

Preferably, the air purge operation is performed repeatedly at predetermined time intervals after the duration of the standby mode has exceeded the predetermined time period.

Preferably, the operation to suck the specimen into the nozzle is performed after the pump has been actuated to suck a predetermined amount of air into the nozzle with a path from the pump to a nozzle opening of the nozzle being fully filled with the cleaning liquid as a result of the air purge operation, to form an air layer between the specimen and the cleaning liquid in the nozzle.

Preferably, the first analyzer is provided with test piece feeding means designed to take a plurality of test pieces stored in a test piece storage unit out of the test piece storage unit one by one and then feed each of the test pieces to a position at which the test piece is spotted with the specimen by the dispenser, the test piece feeding means being capable of preventing the test pieces stored in the test piece storage unit from being exposed to outside during the standby mode by failure to take an unused test piece not spotted with the specimen out of the test piece storage unit.

According to a fourth aspect of the present invention, there is provided an analyzer comprising: a conveyor device capable of conveying a plurality of specimen racks sequentially along a fixed path and feeding the plurality of specimen racks sequentially to a second analyzer in a state of being connected to a downstream side of the analyzer; a dispenser designed to take a specimen out of a container supported on each of the plurality of specimen racks and dispense the specimen to a predetermined portion for analysis; and control means which is capable of data communication with the second analyzer and which establishes a standby mode in which a specimen analyzing operation is suspended temporarily when the second analyzer is determined as being disabled to receive a specimen rack from the conveyor device based on the data communication while a predetermined number of specimen racks are stopped on the conveyor device, wherein:

the dispenser has a nozzle cleaning function capable of supplying a cleaning liquid into a dispensing nozzle after the specimen has been sucked into and discharged from the nozzle by actuating a pump connected to the nozzle; and when the standby mode is established, the dispenser performs an air purge operation for supplying the cleaning liquid into the nozzle by actuating the pump by the time at which the standby mode is released thereafter to cause the dispenser to restart taking the specimen out of the container.

According to a fifth aspect of the present invention, there is provided a connector for use in connecting two conveyor devices for analyzer each having a conveyance track capable of conveying a specimen rack along a fixed path and a frame extending around the conveyance track, the connector comprising opposite end portions, and an upwardly oriented guide surface for slide guiding the specimen rack, wherein when the frames of the two conveyor devices are provided with respective cutouts, the opposite end portions are capable of securely fixed to the frames in such a manner that the upwardly oriented surface is positioned between the cutouts.

Preferably, the connector has an arrangement wherein when the opposite end portions are fixed to the frames of the two conveyor devices for analyzer, interference with a movable member designed to push the specimen rack from a first one of the two conveyor devices toward the other is avoided to allow the movable member to move from the first one to above the guide surface.

Other features and advantages of the present invention will become more apparent from the description of embodiments given below with reference to the accompanying drawings.

BEST MODE FOR CARRYING OUT THE INVENTION

Hereinafter, preferred embodiments of the present invention will be described specifically with reference to the drawings.

Figure 1:
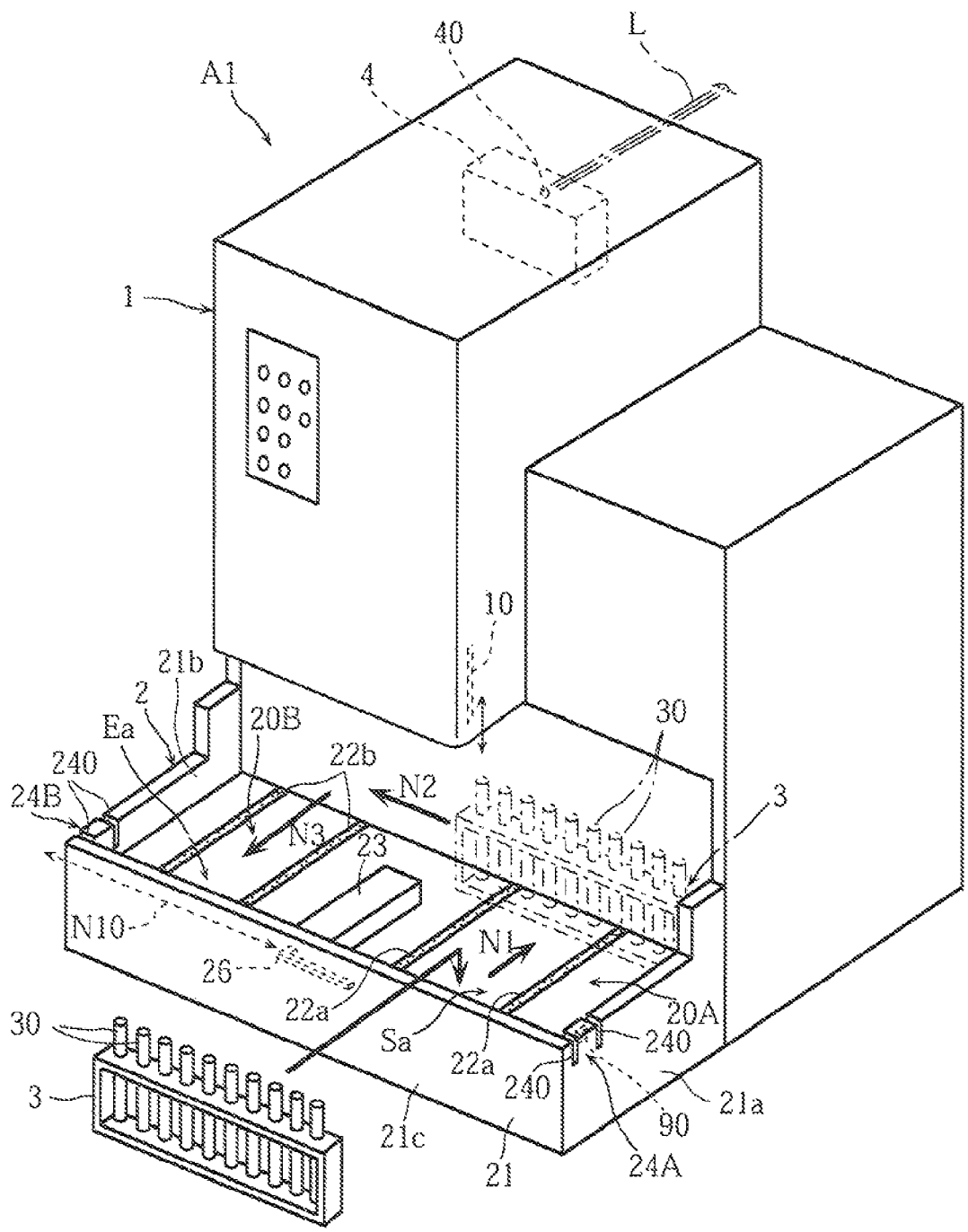
FIG. 1 is a perspective view schematically illustrating an exemplary analyzer according to the present invention.

FIG. 1 illustrates one embodiment of an analyzer according to the present invention. The analyzer A1 according to the present embodiment includes an analyzer body 1 and a conveyor device 2 joined to a lower portion of the analyzer body 1 on the front side.

The analyzer body 1 is capable of measuring the concentration of a specific element in urine, such as hemoglobin, glucose or protein for example, by utilizing a test piece 60 to be described later. When a container 30 containing urine is placed just below a suction nozzle 10 which can move up and down, the analyzer body 1 can perform an operation to measure the concentration of the specific element by sampling the urine from the container 30 by means of the suction nozzle 10.

Figure 3:
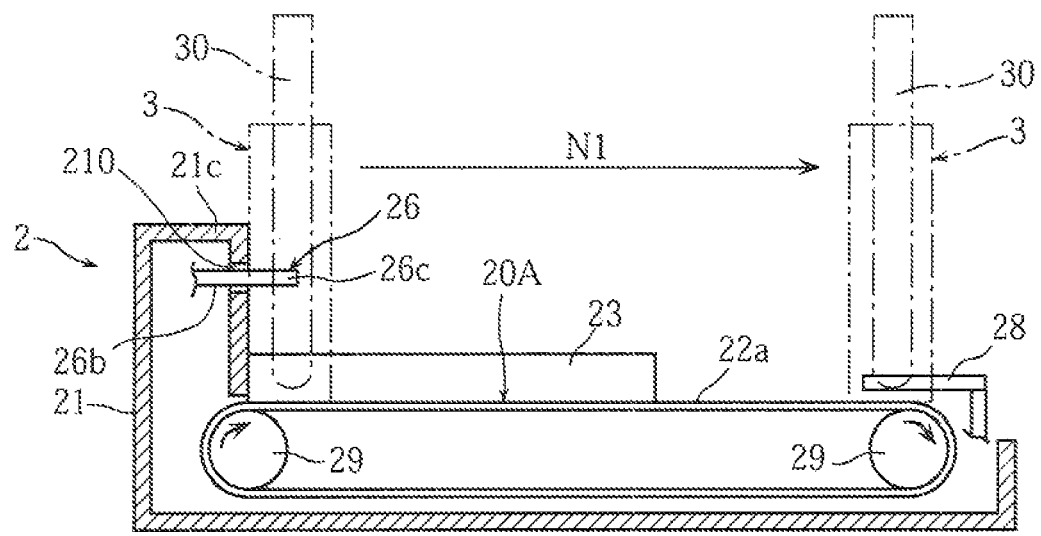
FIG. 3 is a sectional view taken on line III-III of FIG. 2.

The conveyor device 2, which is provided for conveying a specimen rack 3 supporting a plurality of containers 30 in an erected position along a fixed path, includes two conveyance tracks 20A and 20B separated from each other with a partition stand 23, and a frame 21 surrounding the conveyance tracks 20A and 20B on three sides, i.e., the front side and the opposite lateral sides of the conveyance tracks 20A and 20B. The conveyance tracks 20A and 20B each have an upper surface provided with one or more drive belts 22a or 22b, thereby making it possible to convey the specimen rack 3. The driving belts 22a are entrained about a pair of rotatable pulleys 29 as shown in FIG. 3 for example, so that the belts 22a can be driven to circulate along a fixed path. The drive belts 22b are similar in arrangement to the drive belts 22a.

When the specimen rack 3 is fed into a starting area Sa forming the frontmost area of the conveyance track 20A, the conveyor device 2 can convey the specimen rack 3 along a path indicated by arrows N1 to N3. More specifically, the specimen rack 3 is conveyed in the direction of arrow N1 from the starting area Sa to a deeper area of the conveyance track 20A and then conveyed in the direction of arrow N2 by pushing by a pusher 28 shown in FIGS. 2 and 3. During the conveyance by pushing, sampling is performed through the suction nozzle 10. Thereafter, the specimen rack 3 is conveyed on the conveyance track 20B in the direction of arrow N3 to reach an ending area Ea forming the frontmost area of the conveyance track 20B.

The frame 21, which is formed of synthetic resin, includes a front wall portion 21c positioned in front of the conveyance tracks 20A and 20B, and sidewall portions 21a and 21b joined to opposite widthwise ends of the front wall portion 21 and positioned on opposite lateral sides of the conveyance tracks 20A and 20B. The sidewall portions 21a and 21b and the front wall portion 21c have their respective top surfaces which are higher than the top surfaces of the conveyance tracks 20A and 20B. The sidewall portions 21a and 21b are each formed with a pair of slits 240 which define a brittle portion 24A or 24B therebetween. These brittle portions 24A and 24B have their lower portions continuous with the rest of the frame 21. The brittle portions 24A and 24B can be separated and removed from the frame 21 by fracturing their lower portions. The brittle portions 24A and 24B are each an exemplary equivalent of the "separable and removable portion" defined by the present invention and are provided for forming cutouts 25A and 25B, respectively. The cutouts 25A and 25B are an exemplary equivalent of the "first and second cutouts" defined by the present invention. The brittle portion 24A is fitted with a sensor 90 which is capable of detecting the arrival of the specimen rack 3 at the starting area Sa by optical means.

Figure 4:
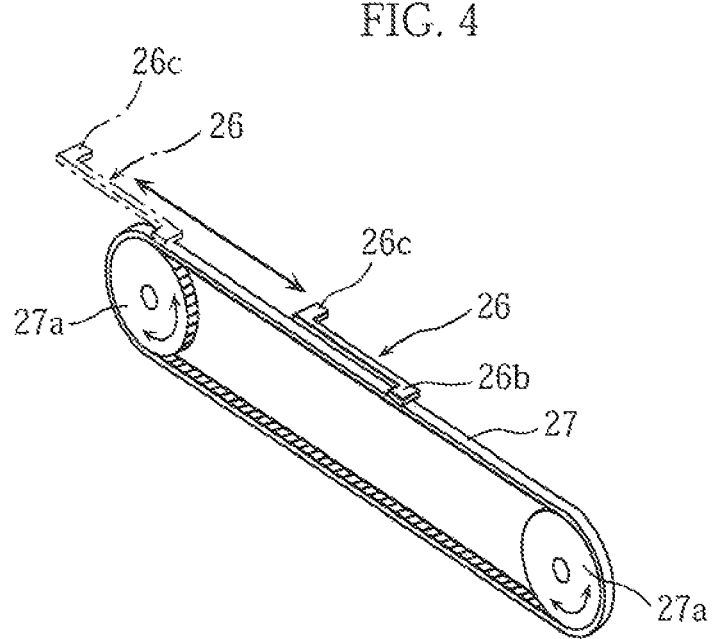
FIG. 4 is a schematic perspective view of a relevant portion for illustrating an exemplary mechanism for driving a pusher shown in FIGS. 1 to 3.

The conveyor device 2 is provided with another pusher 26. As will be described later, in the case where the cutout 25B is formed by separating and removing the brittle portion 24B, the pusher 26 is utilized in discharging the specimen rack 3 positioned in the ending area Ea out of the conveyor device 2. The pusher 26 is reciprocable in the directions of arrow N10 along the front wall portion 21c. As shown in FIG. 4, the pusher 26 has a shape having a base end portion attached to a belt 27 entrained about a pair of pulleys 27a for example and extending from the base end portion 26b in the directions of arrow N10. As the pusher 26 reciprocates, the pusher 26 can move to a position at which its tip portion 26c protrudes from one lateral side of the front wall portion 21c. This feature can enlarge a pushing stroke against the specimen rack 3 and hence is useful in discharging the specimen rack 3 or in a like operation properly, as will be described later. The base end portion 26b of the pusher 26 is located in an internal space of the front wall portion 21c as shown in FIG. 3. On the other hand, the tip portion 26c of the pusher 26 extends through a slit 210 formed in the front wall portion 21c and is exposed to the outside of the front wall portion 21c.

Figure 5:
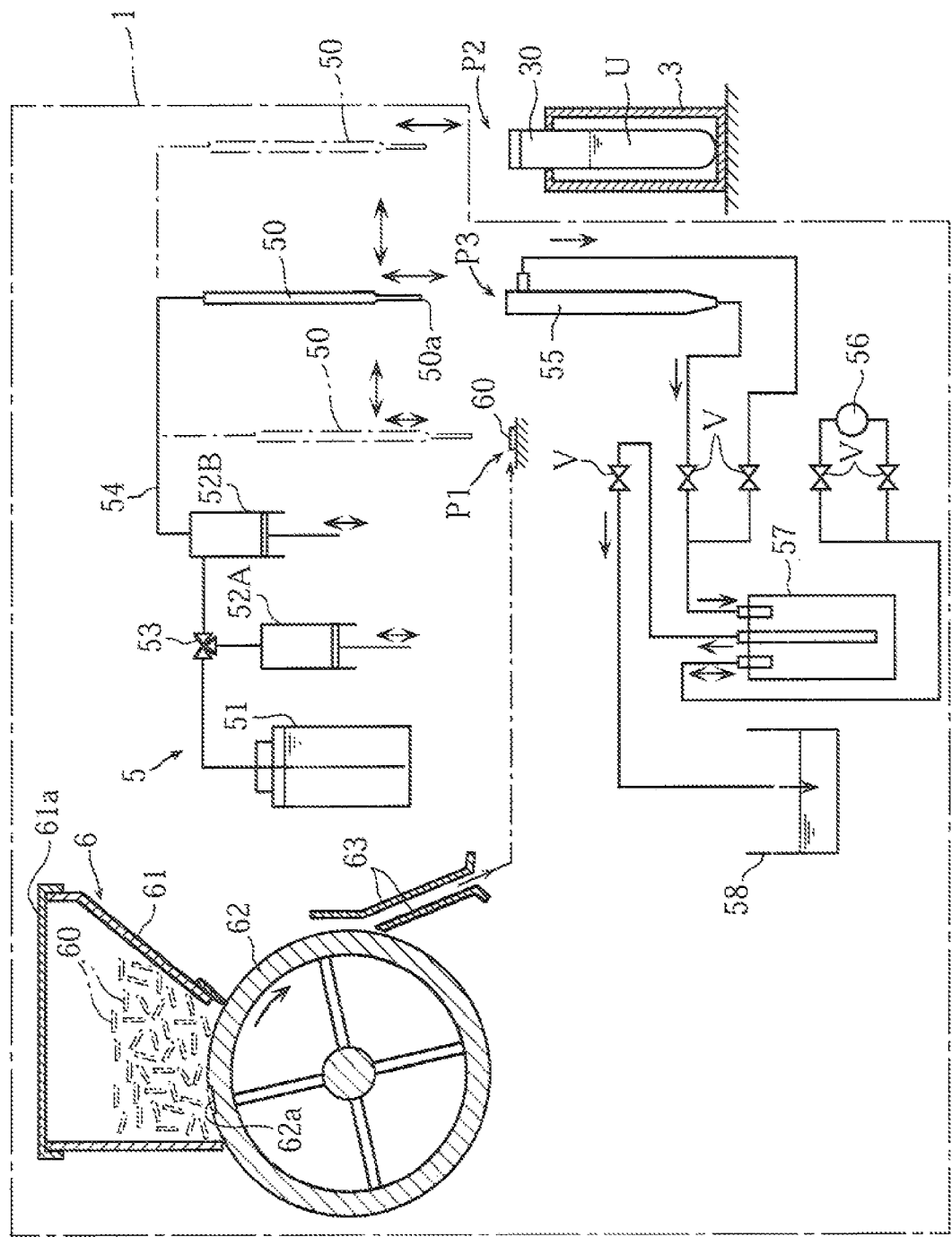
FIG. 5 is an explanatory view schematically illustrating the configuration of an analyzer body shown in FIGS. 1 to 3.

As shown in FIG. 5, the analyzer body 1 includes a dispenser 5 having a nozzle cleaning function, and a test piece feeding device 6.

The test piece feeding device 6, which is provided for feeding a test piece 60 having a reagent portion for analysis of urine to a predetermined position P1, includes a hopper 61 (which is an exemplary equivalent of the "test piece storage unit" defined by the present invention) storing a plurality of test pieces 60 therein, and a rotating drum 62 for taking the test pieces 60 out of the hopper 61 one by one. The hopper 61 is imparted with airtightness to a certain extent by closing its upper opening with a lid 61a and its lower opening with the rotating drum 62 or by a like arrangement and is provided therein with an atmosphere suitable for preventing the test pieces 60 from degrading in quality. The rotating drum 62 has an outer peripheral surface formed with a recess 62a capable of receiving only one test piece 60 therein. As the rotating drum 62 rotates, the test piece 60 fitted in the recess 62a is conveyed to outside the hopper 61 and then introduced between a pair of guides 63. The test piece 60 thus introduced between the pair of guides 63 is transferred by a non-illustrated transfer device to the predetermined position P1 where the reagent portion of the test piece 60 is spotted with the specimen (by dispensing). The analyzer body 1 is provided with measurement means (not shown) for optically measuring a reaction that occurs as a result of the spotting of the reagent portion with the specimen and is designed to determine the concentration of a specific element in the specimen based on the data obtained from the measurement by the measurement means.

The dispenser 5 may have a structure similar to a conventionally known one (as disclosed in Japanese Patent Laid-Open Publication No. 2000-321270 for example) and includes a dispensing nozzle 50, a cleaning liquid tank 51 storing therein a cleaning liquid such as distilled water, syringe pumps 52A and 52B, a directional control valve 53 such as a three-way valve, and a cleaning liquid flow path 54 continuously extending from the cleaning liquid tank 51 to the nozzle 50. The cleaning liquid flow path 54 is formed using an appropriate tube. The nozzle 50 can be moved vertically and horizontally by a non-illustrated actuator or the like and is capable of moving to a position P2 where the specimen is taken out of the specimen rack 3 being conveyed by the conveyor device 2 and to a position P3 where a cleaning vessel 55 is disposed, as well as to the aforementioned position P1.

Figure 11A:
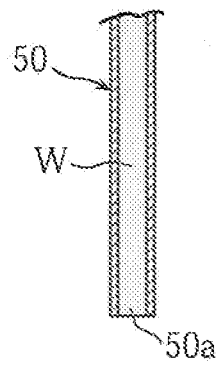
FIGS. 11A to 11C are explanatory views illustrating a series of process steps for sucking a specimen into a dispensing nozzle used in the analyzing system illustrated in FIGS. 6 and 7.
Figure 11B:
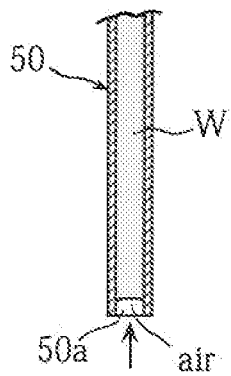
Figure 11C:
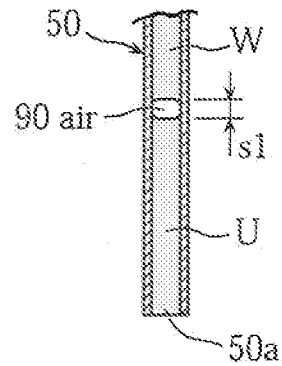

Description is directed to the general operation of the dispenser 5. Initially, the nozzle 50 and the cleaning liquid flow path 54 are entirely filled with the cleaning liquid as an initial setting. This can be achieved by actuating the syringe pump 52A to suck the cleaning liquid from the cleaning liquid tank 51 into the syringe of the syringe pump 52A and then delivering the cleaning liquid toward the nozzle 50. In the initial setting, the inside of the nozzle 50 is filled with cleaning liquid W as shown in FIG. 11A. Subsequently, in sucking the specimen into the nozzle 50, the specimen is sucked after the nozzle 50 has been moved to the position P2. However, immediately before sucking in the specimen the syringe pump 52B is actuated to suck in a very small amount of the cleaning liquid from the nozzle 50 side thereby permitting a slight amount of air to flow into the nozzle 50 as shown in FIG. 11B. This operation causes an air layer 90 to be formed between specimen U and cleaning liquid W in the nozzle 50 as shown in FIG. 11C when the syringe pump 52B is further actuated to cause the nozzle 50 to suck in the specimen. The air layer 90 prevents the cleaning liquid W from being mixed into the specimen U. The operation to spot the test piece 60 with the specimen U is achieved in such a manner that the syringe pump 52B is actuated by a predetermined amount of action after the nozzle 50 has been moved to the position P1, thereby to deliver the specimen U from the nozzle opening 52B.

After the operation of the spotting with the specimen U, the nozzle 50 is subjected to a cleaning operation. The cleaning operation is achieved by moving the nozzle 50 to the position P3 and then actuating the syringe pump 52A to introduce the cleaning liquid into the nozzle 50 in a state of being put into the cleaning vessel 55. By this operation, residual specimen U in the nozzle 50 is discharged to the outside and the interior of the nozzle 50 is cleaned by the cleaning liquid. The exterior of the nozzle 50 is also cleaned by the cleaning liquid supplied into the cleaning vessel 55. The cleaning liquid supplied into the cleaning vessel 55 is fed to a waste liquid tank 58 via an intermediate bottle 57 by switching operations of a pneumatic pump 56 and plural on-off valves V.

The analyzer body 1 includes a control unit 4 configured to perform an operation control required for the aforementioned analyzing operation and a data processing control, as well as a control over the operation of the conveyor device 2. The control unit 4 comprises a CPU and various memory devices, as well as a signal input/output section 40 for data communication with another analyzer through a communication line L. When the analyzer A1 is connected to another analyzer, the control unit 4 is capable of performing a control for causing these analyzers to pass the specimen rack 3 therebetween properly. The details of this control will be described later.

Next, description is directed to the operation of the analyzer A1.

It is needless to say that the analyzer A1 can be used solely without combination with another analyzer. In this case, the analyzer A1 is used with the brittle portions 24A and 24B remaining on the frame 21 as shown in FIG. 1. In this state, the conveyance tracks 20A and 20B are surrounded by the frame 21 on three sides and, hence, any article other than the specimen rack 3 is properly inhibited from inadvertently approaching onto the conveyance tracks 20A and 20B. Further, the conveyance device 2 has a good aesthetic appearance.

Figure 6:
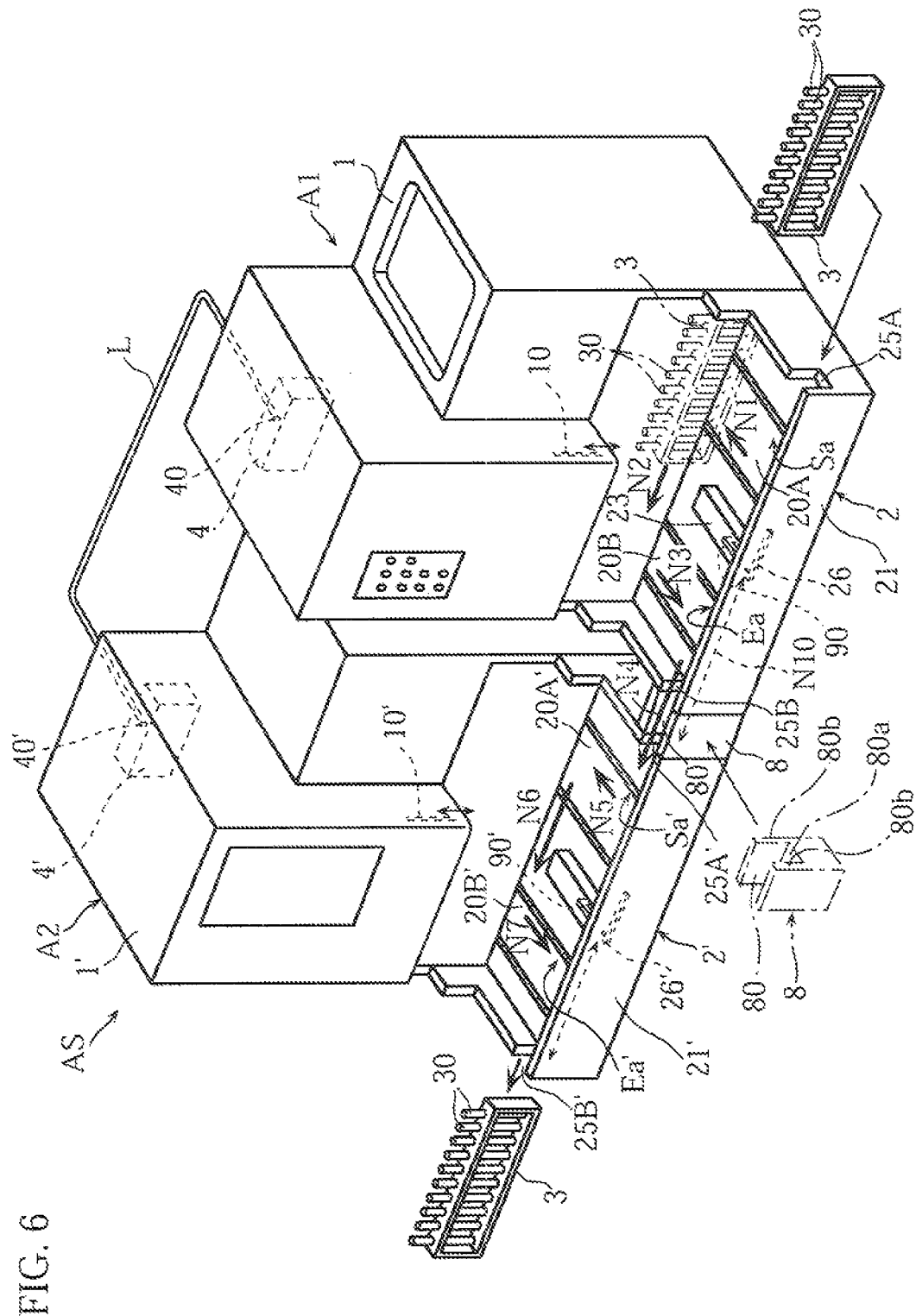
FIG. 6 is a perspective view schematically illustrating an exemplary analyzing system using the analyzer illustrated in FIG. 1.
Figure 7:
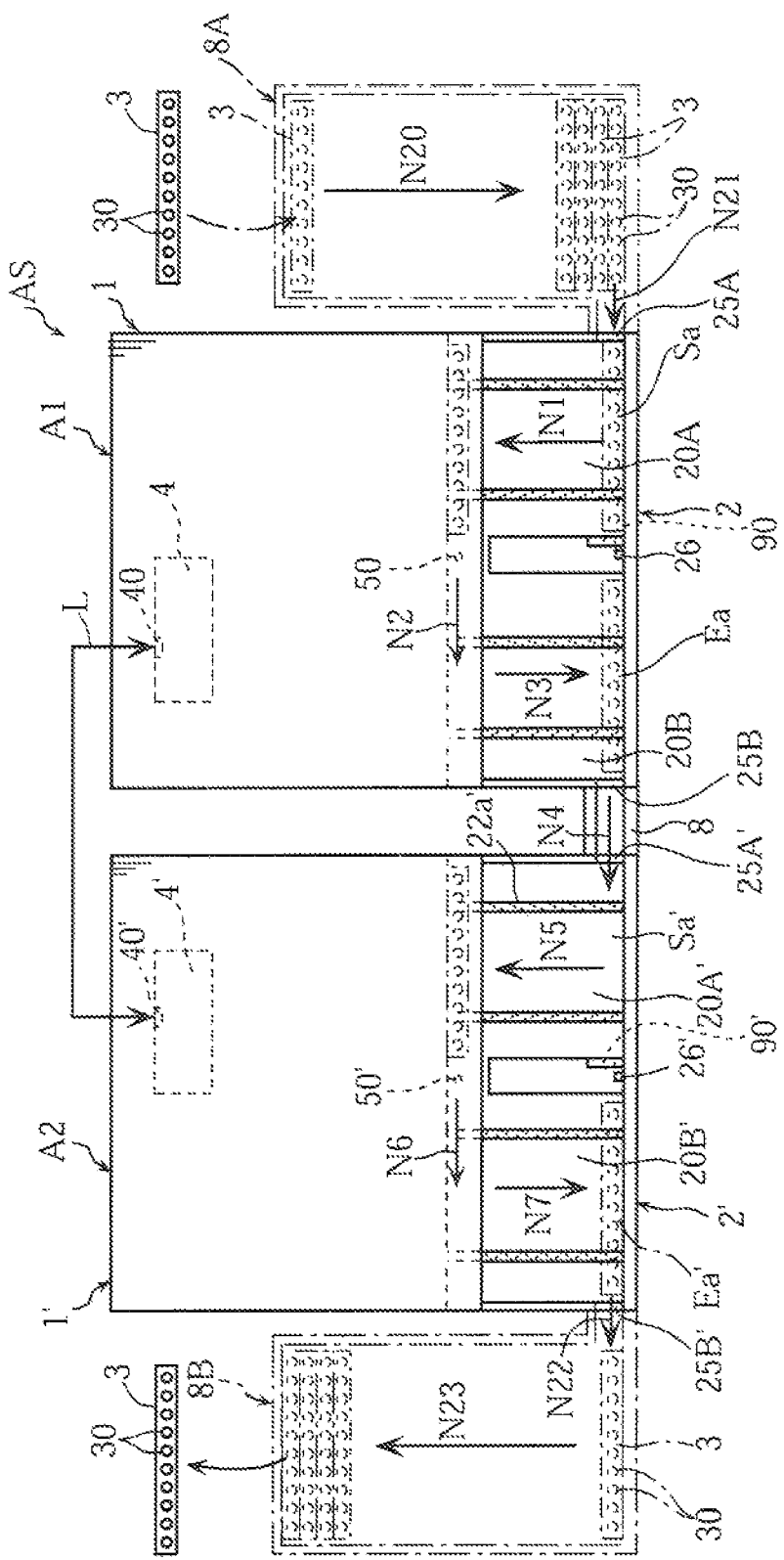
FIG. 7 is a schematic plan view of the analyzing system illustrated in FIG. 6.

In the case where the analyzer A1 is used in combination with another analyzer, an analyzing system AS can be constructed which comprises the analyzer A1 and an analyzer A2 in combination as shown in FIGS. 6 and 7 for example. The analyzer A2 used here is designed to analyze the urine contained in the container 30 for example for an item of analysis that is different from the item of analysis by the analyzer A1 (e.g., analysis of a formed element in urine). The analyzer A2 is also an analyzer according to the present invention and is similar in configuration to the analyzer A1 except the features related directly to the analysis of urine. The parts of the analyzer A2 which are identical with or similar to the corresponding parts of the analyzer A1 are denoted by like symbols with "'" (dash) for the purpose of omitting description thereof.

The analyzing system AS is constructed as follows.

Initially, the conveyor devices 2 and 2' of the respective analyzers A1 and A2 are formed with cutouts 25A and 25B and cutouts 25A' and 25B', respectively, for allowing the specimen rack 3 to pass therethrough. The cutouts 25A and 25B can be easily formed by separating and removing the brittle portions 24A and 24B shown in FIGS. 1 and 2 from the frame 21. The conveyor device 2' is previously provided with brittle portions similar to the brittle portions 24A and 24B and, therefore, the cutouts 25A' and 25B' can be easily formed by removing these brittle portions.

After the removal of the brittle portion 24A from the frame 21, the sensor 90 is removed from the brittle portion 24A and then mounted on an upper portion of the partition stand 23 by utilizing an appropriate bracket. By so doing, the sensor 90 can be reused to detect whether or not the specimen rack 3 is present in the starting area Sa. Preferably, the partition stand 23 has a previously machined portion for mounting the sensor 90 or the bracket supporting the sensor 90 (e.g., a threaded hole for screwing) in order to facilitate the mounting of the sensor 90. This holds true for the sensor 90' of the conveyor device 2'.

Figure 8:
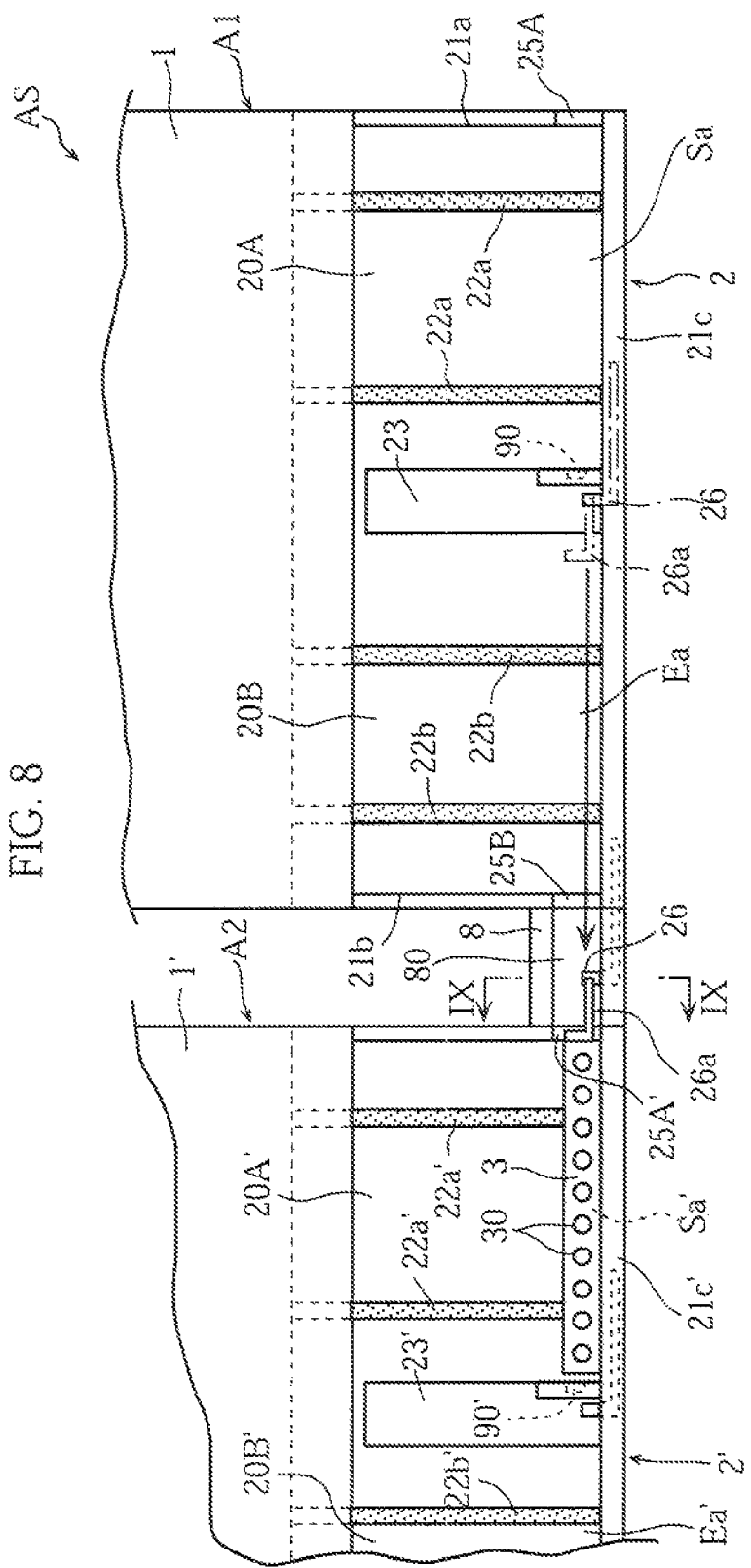
FIG. 8 is a plan view of a relevant portion for illustrating an exemplary operating state of the analyzing system illustrated in FIG. 6.
Figure 9:
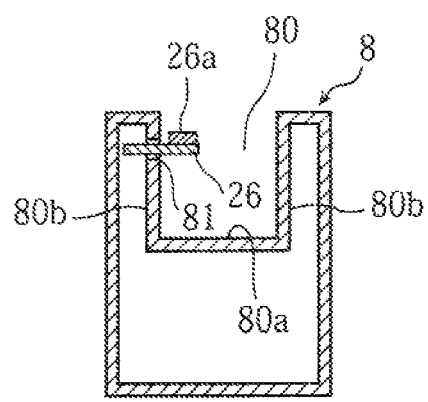
FIG. 9 is a sectional view taken on line IX-IX of FIG. 8.

The conveyor devices 2 and 2' are connected to each other by means of a connector 8. As depicted by a phantom line in FIG. 6, the connector 8 has a recess 80 in an upper portion thereof. The recess 80 is defined by an upwardly oriented guide surface 80a for slide guiding the specimen rack 3 and a pair of opposite sidewalls 80b standing upright from opposite side edges of the guide surface 80a. The connector 8 has opposite ends to be fastened to the frames 21 and 21' of the conveyor devices 2 and 2' by using screwing means. In the fastening, opening portions at the opposite ends of the recess 80 are registered with the cutouts 25B and 25A' without forming a step between the guide surface 80a and the upper surfaces of the conveyance tracks 20B and 20A so that the guide surface 80a bridges the cutouts 25B and 25A'. As shown in FIG. 8, the connector 8 is designed to allow the tip portion of the pusher 26 to advance onto the guide surface 80a. This feature is realized by forming a slit 81 in one sidewall 80b defining part of the recess 80 for allowing the pusher 26 to partially advance into the slit 81 as shown in FIG. 9. The slit 81 is formed for connection to the slit 210 shown in FIG. 3.

As shown in FIG. 7, the conveyor device 2 is connected to an auxiliary conveyor device 8A serving as means for sequentially feeding a plurality of specimen racks 3 toward the starting area Sa through the cutout 25A. The auxiliary conveyor device 8A is designed such that when the plurality of specimen racks 3 are sequentially loaded on its upper surface, these specimen racks 3 are conveyed in the direction of arrow N20 and then made to wait. When the starting area Sa becomes free from specimen rack 3, the specimen racks 3 are fed in the direction of arrow N21 toward the starting area Sa.

The conveyor device 2' is connected to an auxiliary conveyor device 8B for receiving the plurality of specimen racks 3 discharged out of the conveyor device 2' through the cutout 25B'. The auxiliary conveyor device 8B is designed to convey each specimen rack 3 in the direction of arrow N23 immediately after receipt thereof and is capable of storing a plurality of specimen racks 3 thereon.

In the analyzing system AS described above, the conveyance of the specimen rack 3 is performed as follows. Initially, upon arrival of the specimen rack 3 at the starting area Sa from the auxiliary conveyor device 8A, the arrival is detected by utilizing the sensor 90. Thereafter, the specimen rack 3 is conveyed to the ending area Ea along the path indicated by arrows N1 to N3, as already described. Subsequently, the specimen rack 3 is pushed by the pusher 26 in the direction of arrow N4 to reach the starting area Sa' of the analyzer A2 through the cutout 25B, the guide surface 80a of the connector 8 and the cutout 25A'. Since the specimen rack 3 is guided by the connector 8 at that time, the passage of the specimen rack 3 between the analyzers A1 and A2 can be stabilized. As has been described with reference to FIGS. 8 and 9, the pusher 26 advances onto the guide surface 80a of the connector 8 and hence pushes the specimen rack 3 toward the starting area Sa' with a large stroke, thereby making it possible to feed the specimen rack 3 to the starting area Sa' properly. FIGS. 8 and 9 illustrate an arrangement for pushing the specimen rack 3 by utilizing an auxiliary member 26a fitted on the tip portion of the pusher 26. This arrangement ensures proper feeding of the specimen rack 3 to the starting area Sa' by simple means.

In the analyzer A2, specimen racks 3 having been fed to the starting area Sa' are sequentially conveyed along a path indicated by arrows N5 to N7 to reach the ending area Ea'. Each of the specimen racks 3 having reached the ending area Ea' can be properly fed to the auxiliary conveyor device 8B through the cutout 25B' by the operation of the pusher 26'.

As described above, the analyzer A1 can be either suitably used solely or combined with another device, i.e., the analyzer A2 or the auxiliary conveyor device 8A by separating and removing the brittle portions 24A and 24B to form the cutouts 25A and 25B thereby enabling the specimen rack 3 to be properly passed therebetween. Therefore, the analyzer A1 has excellent adaptability for use and does not require replacement of the conveyor device 2 with another conveyor device having a configuration different therefrom when used in combination with another device.

Figure 10A:
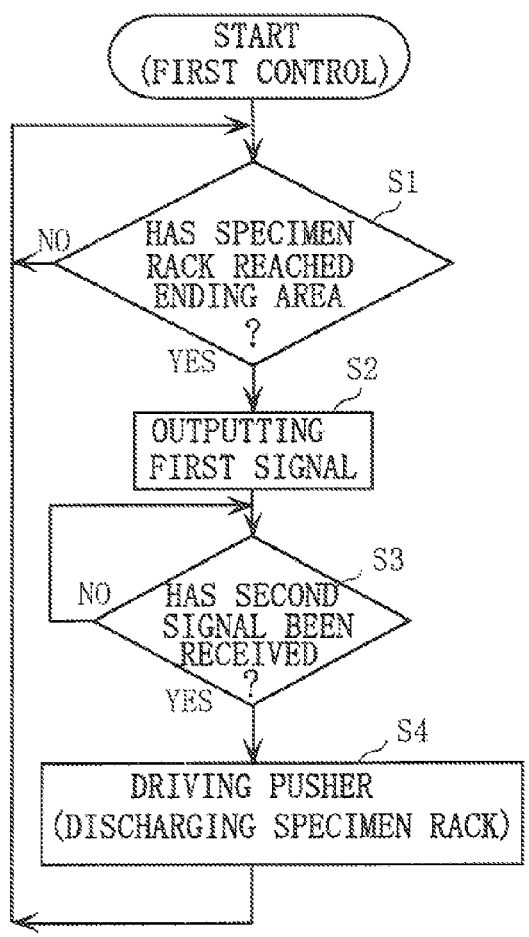
FIGS. 10A and 10B are flowcharts of exemplary operation control processes carried out by the analyzing system illustrated in FIGS. 6 and 7.
Figure 10B:
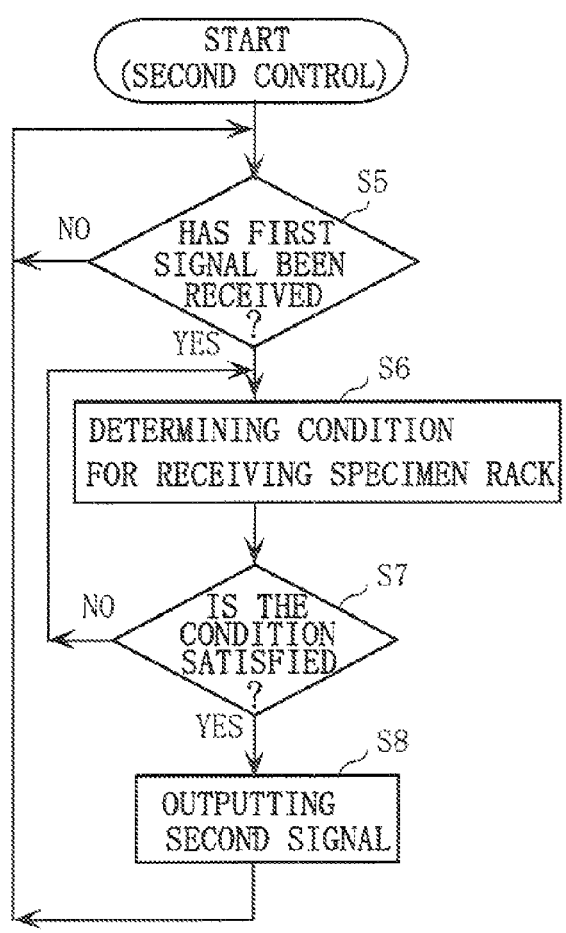

In passing the specimen rack 3 between the analyzers A1 and A2, the control unit 4 performs a first control as illustrated in FIG. 10A, while the control unit 4' performs a second control as illustrated in FIG. 10B. The details of these controls are described below.

Initially, in response to detection of arrival of the specimen rack 3 at the ending area Ea by a predetermined sensor (not shown), the control unit 4 outputs a first signal from the signal input/output section 40 to inform the control unit 4' of the arrival (S1: YES, S2). Subsequently, the control unit 4 keeps the pusher 26 waiting until the signal input/output section 40 receives a second signal responding to the first signal (S3: NO). Upon receipt of the second signal, the control unit 4 actuates the pusher 26 (S3: YES, S4). This causes the specimen rack 3 to be fed from the ending area Ea of the analyzer A1 to the starting area Sa' of the analyzer A2.

On the other hand, in response to the first signal received from the control unit 4, the control unit 4' determines whether or not a condition for receiving the specimen rack 3 is satisfied (S5: YES, S6). Examples of such conditions for reception include a condition in which a specimen rack 3 is absent in the starting area Sa' while the belt 22a' of the conveyance track 20A' inclusive of the starting area Sa' is in a stopped state. If the condition for reception is not satisfied, the control unit 4' refrains from outputting the second signal (S7: NO). At the time the condition has been satisfied, the control unit 4' outputs the second signal to the control unit 4 (S7: YES, S8).

According to the above-described controls, on condition that after the specimen rack 3 has reached the ending area Ea of the analyzer A1, any other specimen rack 3 is not present in the staring area Sa' of the analyzer A2 while the belt 22a' is in the stopped state, the specimen rack 3 can be quickly fed to the starting area Sa'. In the case where a specimen rack 3 is present in the starting area Sa', if the pusher 26 is actuated to feed another specimen rack 3 to the starting area Sa', it is possible that these specimen racks 3 collide with each other, which might result in occurrence of a failure. If the specimen rack 3 is fed while the belt 22a' of the analyzer A2 is driven, it is possible that the leading end portion of the specimen rack 3 is moved in the direction of arrow N5 upon stepping onto the belt 22a', which might cause the specimen rack 3 to be skewed. Such problems can be properly avoided by the controls described above.

Figure 2:
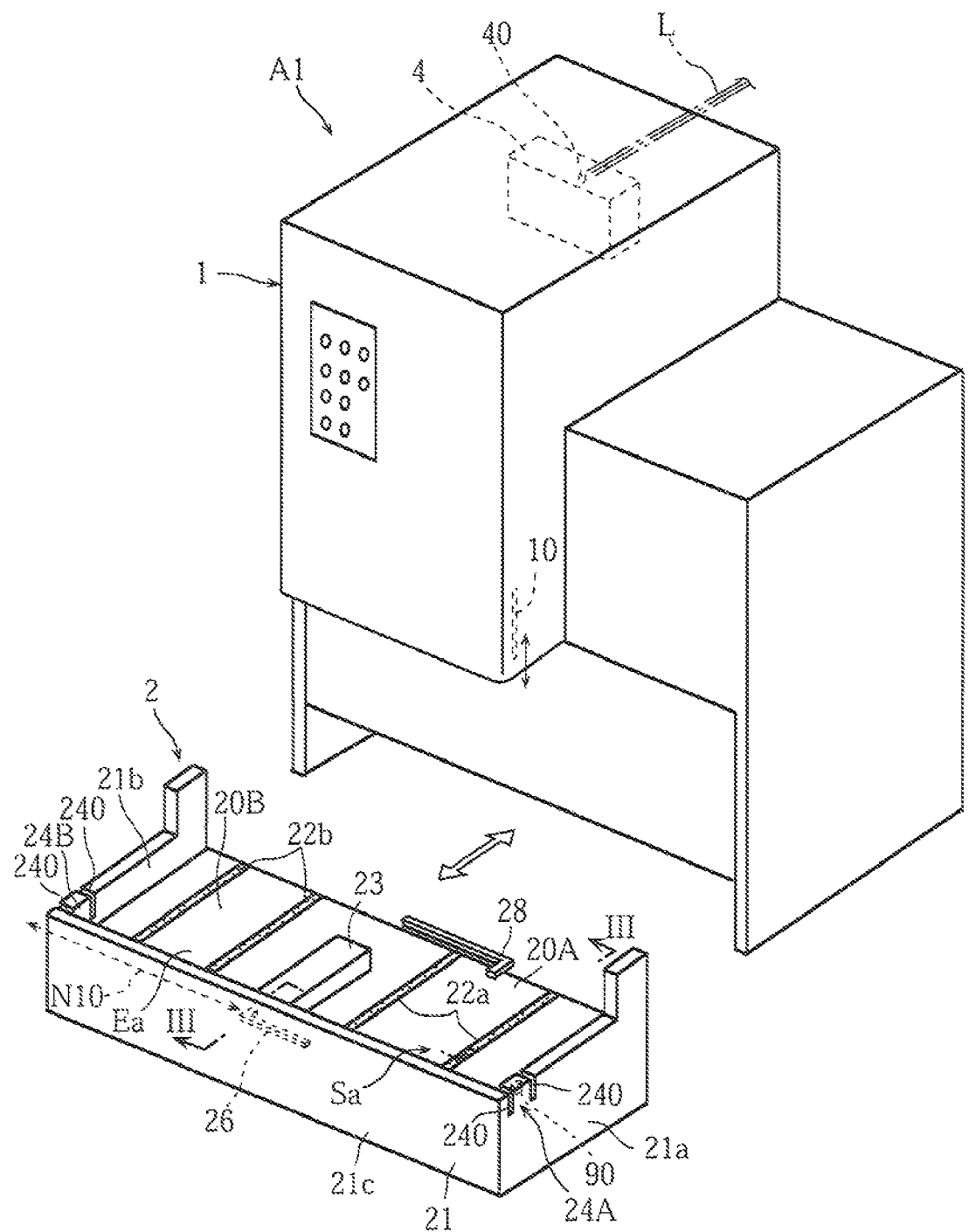
FIG. 2 is an exploded perspective view of the analyzer illustrated in FIG. 1.

The control units 4 and 4' are each capable of performing both of the first and second controls illustrated in FIGS. 10A and 10B and are each provided with control programs therefor. Therefore, even a system in which the analyzer A1 is connected to the downstream side of the analyzer A2 unlike in the analyzing system AS illustrated in FIGS. 2 and 3, can obtain the advantage that the analyzers A1 and A2 can pass the specimen rack 3 therebetween with appropriate timing as does the above-described analyzing system AS.

Figure 14:
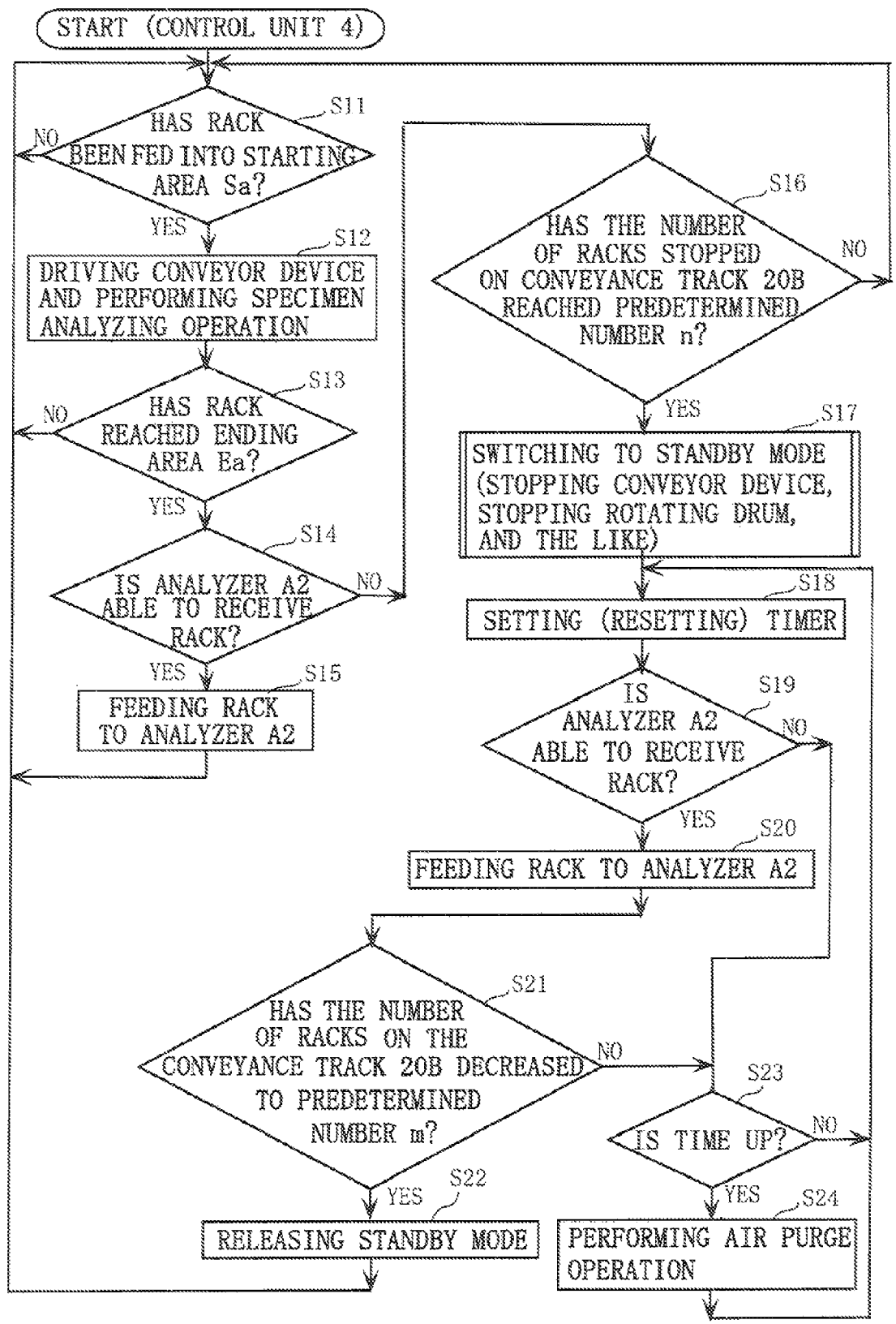
FIG. 14 is a flowchart of an exemplary operation control performed by a control unit of a first analyzer included in the analyzing system illustrated in FIGS. 6 and 7.

The control unit 4 of the analyzer A1 is configured to perform also an operation control as illustrated in the flowchart of FIG. 14. This operation control is as follows.

The operation to repeat steps S11 to S15 of the flowchart of FIG. 14 has been already described and, therefore, description thereof will be omitted. In the case where the analyzing speed of the analyzer A2 is lower than that of the analyzer A1, the analyzer A2 becomes disabled to receive a specimen rack 3 from the analyzer A1 when a certain time period has elapsed from the start of operation even though the analyzers A1 and A2 operate normally (S14: NO). This situation is a situation in which even though a specimen rack 3 has reached the ending area Ea of the conveyor device 2A, a specimen rack 3 in the starting area Sa' of the conveyor device 2B has not been conveyed in the direction of arrow N5 yet. Even under such a situation, the analyzer A1 does not stop immediately but keeps on conveying specimens sequentially fed to the starting area Sa and analyzing these specimens, so that a plurality of specimen racks 3 are sequentially stored on the conveyance track 20B of the conveyor device 2A. When the number of specimen racks 3 thus stored reaches a predetermined number "n", the control unit 4 switches the analyzer A1 to a standby mode to suspend the analyzing operation (S14: NO, S16: YES, S17). Here, the predetermined number "n" may be any number of specimen racks that can be stored on the conveyance track 20B. It is possible to set the number "n" to "1" as a minimum number.

In establishing the aforementioned standby mode, it is not appropriate to suspend the analyzing operation in progress. For this reason, the standby mode is established with such timing as not to cause the suspension. In the test piece feeding device 6 shown in FIG. 5, the rotating drum 62 is stopped to stop taking a test piece 60 out of the hopper 61. When some test pieces 60 have already been taken out of the hopper 61, the standby mode is established after the analyzing operation using these test pieces 60 has been completed. By so doing, unused test pieces 60 are prevented from being exposed to outside of the hopper 61 for a prolonged time and hence can be prevented from degrading in quality.

Upon establishment of the standby mode, the control unit 4 sets a timer for measuring the duration of the standby mode (S18). Thereafter, when the analyzer A2 becomes able to receive specimen racks 3, the specimen racks 3 are sequentially fed to the analyzer A2, so that the number of specimen racks 3 stored on the conveyance track 20B decreases to a predetermined number "m". At that time, the control unit 4 releases the standby mode and causes the analyzer A1 to resume the specimen analyzing operation (519: YES, S20, S21: YES, S22). The predetermined number "m" is any number which is less than the aforementioned predetermined number "n" and may be zero.

Figure 12A:
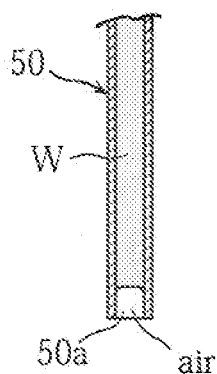
FIGS. 12A and 12B are explanatory views illustrating an air purge operation process carried out in a standby mode of the analyzing system illustrated in FIGS. 6 and 7.
Figure 12B:
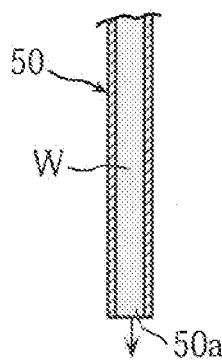

At the time when the time set on the aforementioned timer is up because the predetermined duration of the standby mode has elapsed without the standby mode released, the control unit 4 causes the dispenser 5 to perform an air purge operation (S19: NO, S21: NO, S23: YES, S24). The air purge operation includes: sucking the cleaning liquid from the cleaning liquid tank 51 into the syringe of the syringe pump 52A shown in FIG. 5 by actuating the syringe pump 52A; and then delivering the cleaning liquid from the syringe toward the dispensing nozzle 50. In this case the amount of cleaning liquid to be delivered into the nozzle 50 is an amount to such an extent as to cause the nozzle 50 to spout some amount of cleaning liquid, thereby to ensure that the inside of the nozzle 50 is fully filled with the cleaning liquid. As the standby mode continues over a certain time period, the cleaning liquid in the nozzle 50 evaporates, which might allow air to flow into the nozzle 50 as shown in FIG. 12A. The air purge operation serves to purge such air out of the nozzle 50 and, as a result of the air purge operation, the inside of the nozzle 50 becomes fully filled with the cleaning liquid as shown in FIG. 12B.

Figure 13A:
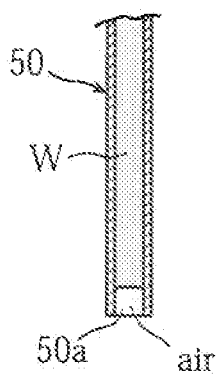
FIGS. 13A to 13C are explanatory views illustrating a comparative example for comparison with the embodiment of the present invention illustrated in FIGS. 11A to 11C.
Figure 13B:
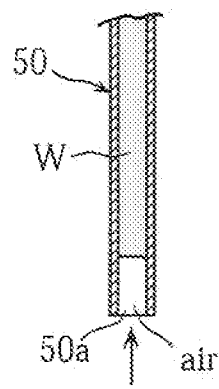
Figure 13C:
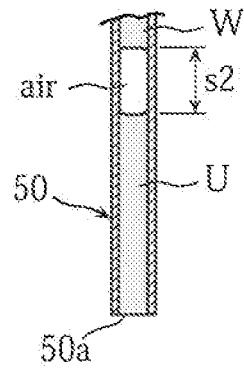

The above-described air purge operation makes it possible to dispense the specimen appropriately during the specimen analyzing operation resumed by the release of the standby mode after the air purge operation. This will be described using a comparative example illustrated in FIGS. 13A to 13C. With air in the nozzle 50 as shown in FIG. 13A due to evaporation of the cleaning liquid during the standby mode, the nozzle 50 is caused to suck in air in a little amount and then suck in specimen U as shown in FIGS. 13B and 13C and, as a result, there is formed an air layer having a length s2 which is pretty larger than the length s1 of the air layer 90 shown in FIG. 11C. With increasing volume of an air layer, an error becomes more likely in the amount of delivery of the cleaning liquid. Accordingly, with the comparative example illustrated in FIGS. 13A to 13C, an error is likely in the amount of specimen U to be dispensed from the nozzle 50 for spotting a test piece 60 with specimen U. By contrast, the present embodiment has a low possibility of such a problem and can suck in the specimen in the manner illustrated in FIGS. 11A to 11C, thereby obtaining the advantage that the test piece 60 can be spotted with an accurate amount of specimen U.

In the present embodiment, the air purge operation is performed only when the standby mode continues for the predetermined duration or longer. Stated otherwise, the air purge operation is not performed in the case where the standby mode duration is short and, hence, there is substantially no possibility of intrusion of air into the dispensing nozzle 50. For this reason, the air purge operation is performed effectively and, hence, the consumption of the cleaning liquid can be reduced. The present invention may be embodied such that the air purge operation is performed every time the standby mode is established, unlike the present embodiment.

According to the present embodiment, in the case where the timer is reset after the air purge operation and the time set on the timer is up again because the standby mode continues further, the air purge operation is performed again (S24, S18, S19: NO, S23:YES). That is, in the case where the standby mode continues for a prolonged duration, the air purge operation is performed at fixed time intervals. This is more preferable in lowering the possibility that air is present in the nozzle 50 at the time of release of the standby mode. With respect to the air purge timing, the present invention may be embodied such that the air purge operation is performed with a timing different from that in the present embodiment, for example, at the time immediately before the operation to suck in the specimen U (immediately before the operation illustrated in FIG. 11B).

FIGS. 15 to 18 illustrate other embodiments of the present invention. In these figures, parts which are identical with or similar to the corresponding parts of the foregoing embodiment are denoted by like symbols.

Figure 15A:
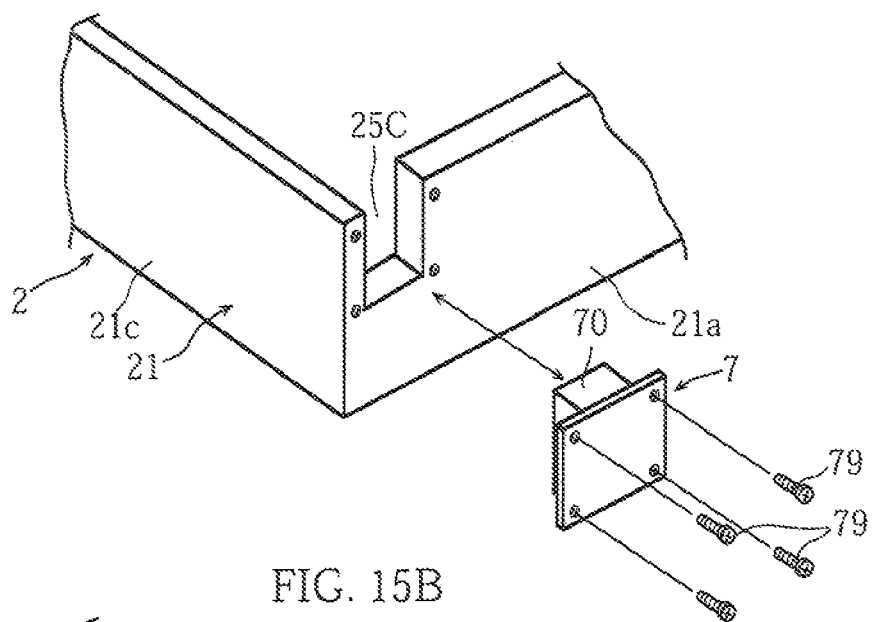
FIGS. 15A and 15B are perspective views of a relevant portion for illustrating another embodiment of the present invention.
Figure 15B:
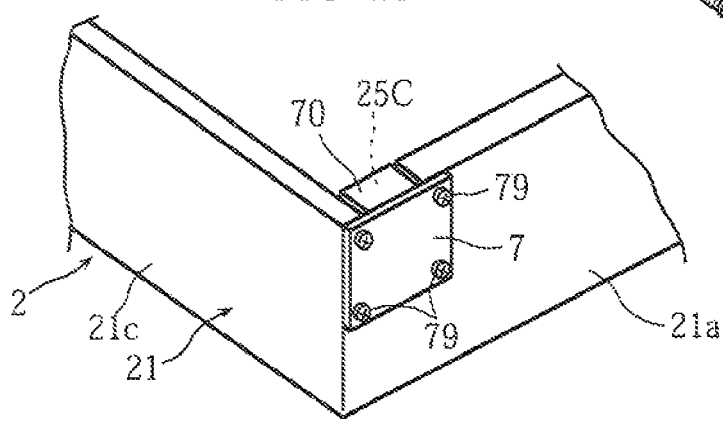

In the embodiment illustrated in FIGS. 15A and 15B, the sidewall portion 21a of the frame 21 in the conveyor device 2 is previously formed with a cutout 25C. The cutout 25C is closed with a closing member 7. The closing member 7, which is another exemplary equivalent of the separable and removable portion defined by the present invention, is mounted on the frame 21 by means of screws 79 for example. Preferably, the closing member 7 has a fitting portion 70 to be fitted into the cutout 25A and is designed to close the cutout 25C in such a manner as to provide a good aesthetic appearance.

According to the present embodiment, in the case where the conveyor device 2 is used without being connected to another conveyor device, the cutout 25C is kept closed with the closing member 7 as shown in FIG. 15B. On the other hand, in the case where the conveyor device 2 is used as connected to another device, the closing member 7 is removed to open the cutout 25C as shown in FIG. 15A, thereby allowing a specimen rack to pass therethrough. Therefore, like the foregoing embodiment, the present embodiment can suitably accommodate to both of the cases where an analyzer provided with the conveyor device 2 is used solely and where the analyzer is used as connected to another analyzer.

Figure 16:
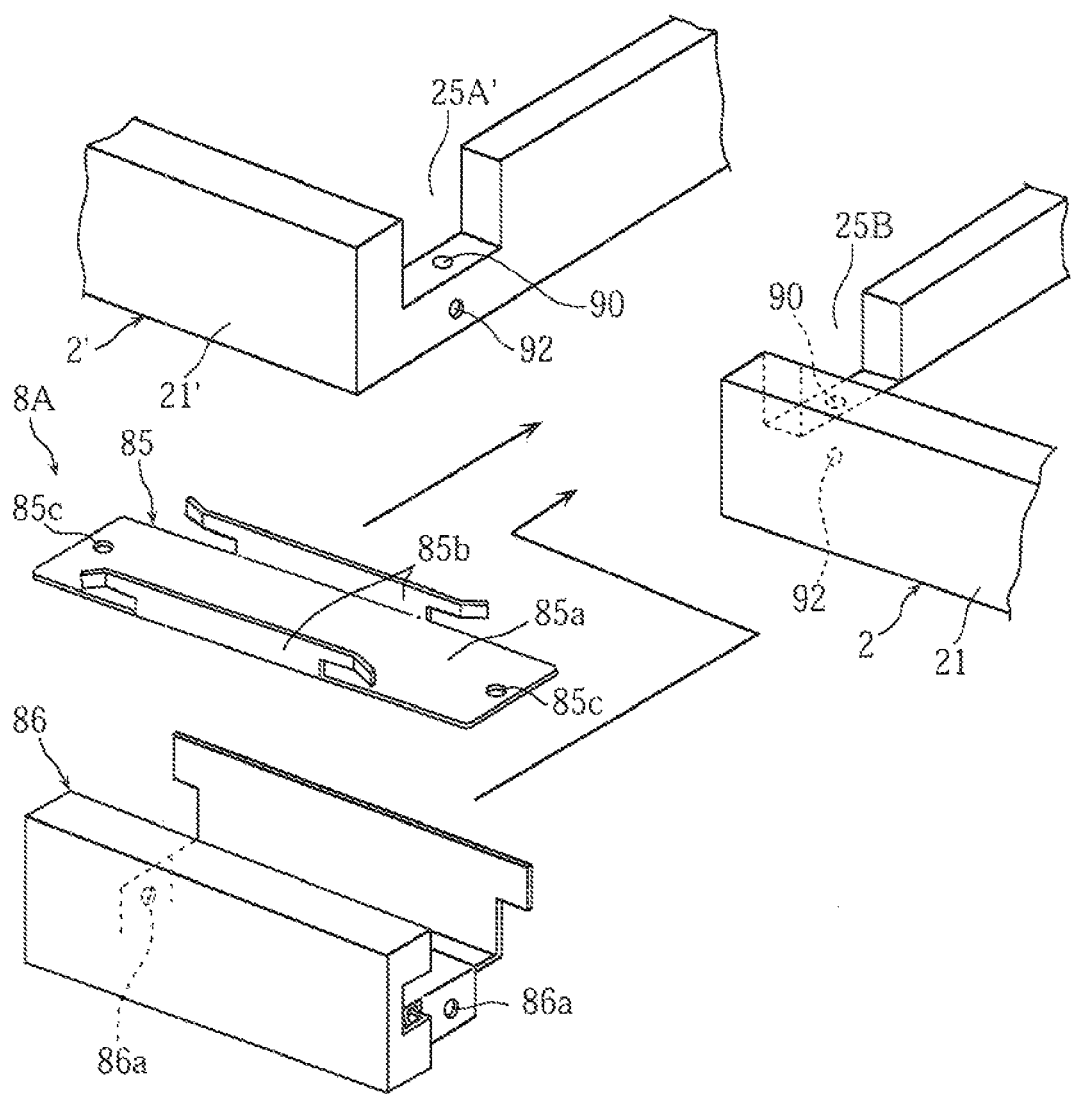
FIG. 16 is an exploded perspective view illustrating another embodiment of the present invention.
Figure 17:
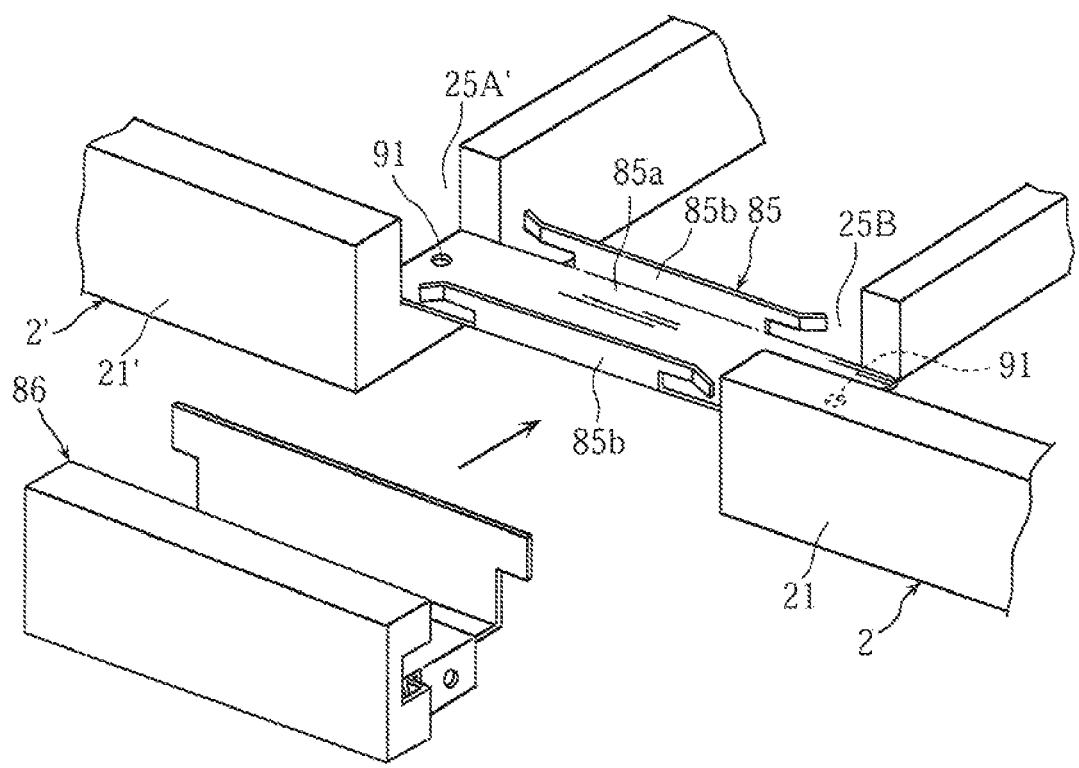
FIG. 17 is a perspective view of a relevant portion for illustrating an intermediate state in assembling the member shown in FIG. 16 with a conveyor device for analyzer.
Figure 18:
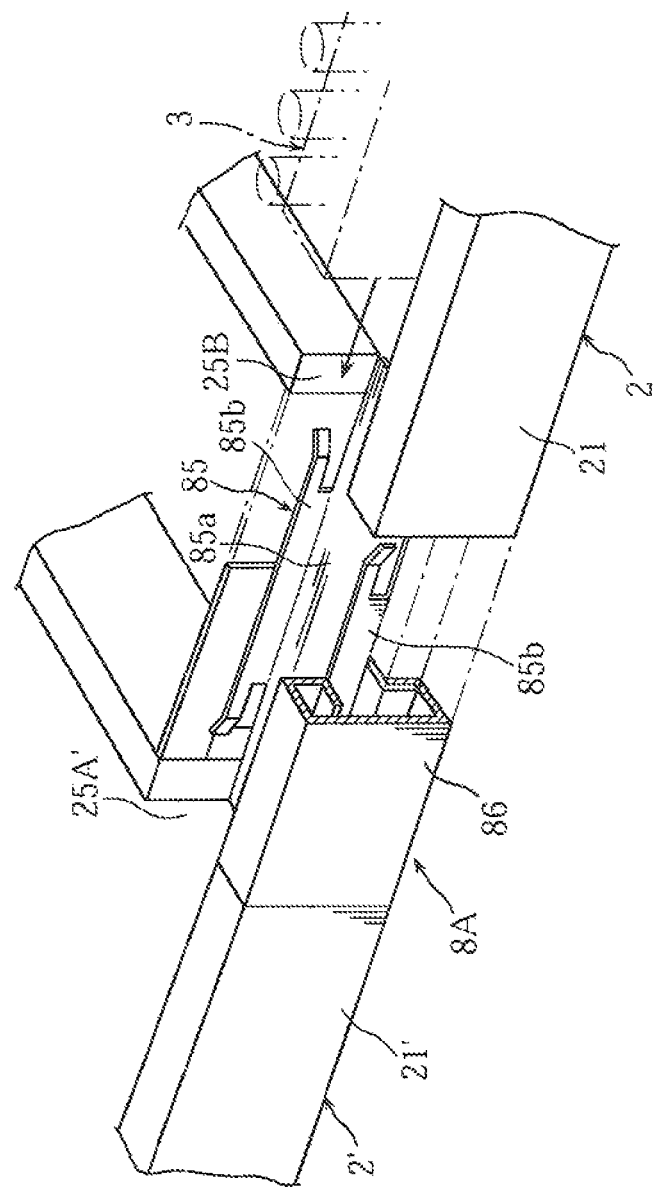
FIG. 18 a partially cutaway perspective view, partially in section, of a relevant portion for illustrating a state in which the member shown in FIG. 16 has been assembled with the conveyor device for analyzer.

In the embodiment illustrated in FIGS. 16 to 18, a connector 8A comprises a connector body 85 and a decorative cover 86. The connector body 85 is formed by press working a relatively thin metal sheet and has an upwardly oriented guide surface 85a for slide guiding a specimen rack 3 and a pair of opposite sidewalls 85b standing upright from opposite side edges of the guide surface 85a. The connector body 85 has opposite end portions formed with respective screw receiving holes 85c coinciding with threaded holes 90 formed in the frames 21 and 21' of the conveyor devices 2 and 2'. By utilizing screws 91, the connector body 85 can be mounted so as to bridge the cutouts 25B and 25A' of the conveyor devices 2 and 2', as shown in FIG. 17. The decorative cover 86 is provided for the purpose of preventing the connector body 85 from being seen unaesthetically from outside. As shown in FIG. 18, the decorative cover 86 is interposed between sidewall portions of the frames 21 and 21' to cover part of the periphery of the connector body 85 so as not to hinder the guiding of the specimen rack 3 by the connector body 85. The decorative cover 86 has opposite end portions provided with holes 86a coinciding with threaded holes 92 formed in the sidewall portions of the frames 21 and 21' (see FIG. 16). The decorative cover 86 can be mounted on the frames 21 and 21' by threadingly engaging a screw (not shown) into each pair of hole 86a and threaded hole 92.

According to the connector 8A, the connector body 85 for guiding a specimen rack 3 being conveyed can be easily formed by press working a metal sheet to have, as a whole, a high dimensional precision and a sufficient durable strength. Since the connector body 85 is mostly covered and hidden with the decorative cover 86, the connector 8A can be wholly improved in aesthetic appearance.

The present invention is not limited to the foregoing embodiments. The specific structure of each part of the conveyor device for analyzer according to the present invention and the specific structure of each part of the analyzer according to the present invention can be modified in design in various ways.

The "separable and removable portion", as defined by the present invention, may be a portion of the frame which is rendered easy to fracture by reducing the wall thickness of the frame partially or modifying the material of the frame partially for example, instead of the portion of the frame which is rendered brittle by forming slits in the frame. The specific size and position of the separable and removable portion may be variously changed to meet the specific structure of the conveyance tracks of the conveyor device. Though it is preferable to provide at least two such separable and removable portions to enable other devices to be connected to the upstream side and the downstream side, respectively, of the conveyor device for allowing the specimen rack to be passed between the conveyor device and the other devices, the present invention is not limited to this arrangement. The technical scope of the present invention also encompasses an arrangement provided with only one separable and movable portion for example.

The analyzer according to the present invention is not limited to an analyzer designed to measure the concentration of a specific element in urine, but may be an analyzer designed to measure the concentration of a specific element in blood, for example, the concentration of glucose, glycohemoglobin or other specific element in blood. There is no limitation on the type of a specific specimen or on the details of the analyzing operation. In the analyzing system according to the present invention, the number of analyzers connected to each other is not limited to two, but may be three or more. The "test piece storage unit", as defined by the present invention, may have a structure selected from various structures including a hopper-shaped structure having a bottom portion defining a test piece outlet and a box-shaped structure having a closed bottom portion. Further, it is possible to use the rotating drum or other various devices as specific means for taking test pieces out of the test piece storage unit one by one. In general, the "test piece" is meant by a piece which comprises an appropriate base material and a reagent applied to the base material and which enables a specimen to be analyzed based on changes in the color of the reagent. However, the "test piece", as defined by the present invention, is not limited thereto. The "test piece" according to the present invention is meant by a concept including, for example, such a test piece which comprises a reagent portion and electrodes connected to the reagent portion and is capable of detecting the condition of reaction between the specimen and the reagent. Of course, it does not matter whether or not the test piece is of disposable type.

The invention claimed is:

1. A conveyor device for analyzer comprising:
   a conveyance track capable of conveying a specimen rack along a fixed path; and
   a frame positioned around the conveyance track,
   the frame being provided with a separable and removable portion which is separable and removable from the frame and which is capable of providing the frame with a cutout in open condition when separated and removed from the frame,
   wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout,
   wherein the conveyance track has a starting area located close to a first widthwise end of the frame and an ending area located close to an opposite second widthwise end of the frame;
   the separable and removable portion is provided at each of the first and second widthwise ends of the frame to enable a first cutout to be formed at the first widthwise end of the frame for allowing the specimen rack to advance therethrough into the starting area from a first outer lateral side of the frame and enable a second cutout to be formed at the second widthwise end of the frame for allowing the specimen rack to be discharged therethrough from the ending area to a second outer lateral side of the frame.

2. The conveyor device for analyzer according to claim 1, wherein:
   the frame is provided with a pair of vertically extending slits which are horizontally spaced apart from each other to provide a brittle portion of the frame therebetween; and
   the brittle portion forms the separable and removable portion.

3. The conveyor device for analyzer according to claim 1, wherein:
   the frame is fitted with a separate and removable closing member in such a manner as to close a cutout previously formed in the frame; and
   the closing member forms the separable and removable portion.

4. The conveyor device for analyzer according to claim 1, further comprising a connector which is capable of connecting the frame to another conveyor device for analyzer and which has an upwardly oriented guide surface capable of guiding the specimen rack being conveyed through the first cutout or the second cutout when the connector is in a connecting state.

5. The conveyor device for analyzer according to claim 4, further comprising a movable member which is reciprocable widthwise of the frame at a location adjacent the ending area,
   the movable member being capable of moving the specimen rack having been conveyed into the ending area toward the second cutout.

6. The conveyor device for analyzer according to claim 5, wherein the movable member is capable of advancing onto the guide surface from the ending area side when the connector is connected to the frame to guide the specimen rack passing through the second cutout.

7. A conveyor device for analyzer comprising:
   a conveyance track capable of conveying a specimen rack along a fixed path; and
   a frame positioned around the conveyance track, the frame being provided with a separable and removable portion which is separable and removable from the frame and which is capable of providing the frame with a cutout in open condition when separated and removed from the frame,
   wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout, wherein:
   the separable and removable portion is fitted with a sensor for detecting whether or not the specimen rack is present at a predetermined point; and
   when the separable and removable member is separated and removed from the frame, the sensor is allowed to be removed from the separable and removable member and then placed adjacent the predetermined point for reuse in determination as to whether or not the specimen rack is present at the predetermined point.

8. An analyzer comprising a conveyor device,
   the conveyor device comprising:
   a conveyance track capable of conveying a specimen rack along a fixed path; and a frame positioned around the conveyance track, the frame being provided with a separable and removable portion which is separable and removable from the frame and which is capable of providing the frame with a cutout in open condition when separated and removed from the frame, wherein when the frame is provided with the cutout in open condition, the cutout allows at least one of an operation to advance the specimen rack onto the conveyance track from an outer lateral side of the frame through the cutout and an operation to discharge the specimen rack from the conveyance track to outside of the frame through the cutout;

the analyzer further including:

an analyzer body capable of analyzing a specimen;

a conveyor device capable of conveying the specimen rack having been fed into a predetermined starting area toward the analyzer body or a location adjacent thereto and then conveying the specimen rack to a predetermined ending area; and control means having a signal input/output section capable of data communication with another analyzer, the control means being configured to carry out a process including:

outputting a predetermined first signal from the signal output/input section to outside in response to arrival of a specimen rack at the ending area; instructing the conveyor device to perform an operation to discharge the specimen rack from the ending area to outside of the conveyor device in response to receipt of a predetermined second signal by the signal input/output section from outside after the outputting of the first signal;

determining whether or not a predetermined condition for receiving a specimen rack into the starting area is satisfied in response to receipt of the first signal by the signal input/output section from outside; and outputting the second signal from the signal input/output section in response to a determination that the predetermined condition is satisfied.

9. The analyzer according to claim 8, wherein the predetermined condition is a condition in which any specimen rack is not present in the starting area of the conveyor device while the starting area is in a stationary condition incapable of conveying a specimen rack.

10. A connector for use in connecting two conveyor devices for analyzer each having a conveyance track capable of conveying a specimen rack along a fixed path and a frame extending around the conveyance track, the connector comprising opposite end portions, and an upwardly oriented guide surface for slide guiding the specimen rack, wherein when the frames of the two conveyor devices are provided with respective cutouts, the opposite end portions are capable of securely fixed to the frames in such a manner that the upwardly oriented surface is positioned between the cutouts, wherein when the opposite end portions are fixed to the frames of the two conveyor devices for analyzer, interference with a movable member designed to push the specimen rack from a first one of the two conveyor or devices toward the other is avoided to allow the movable member to move from the first one to above the guide surface.

* * * * *